United States Patent
Ukil et al.

(10) Patent No.: US 11,589,760 B2
(45) Date of Patent: Feb. 28, 2023

(54) SYSTEM AND METHOD FOR PHYSIOLOGICAL MONITORING AND FEATURE SET OPTIMIZATION FOR CLASSIFICATION OF PHYSIOLOGICAL SIGNAL

(71) Applicant: Tata Consultancy Services Limited, Mumbai (IN)

(72) Inventors: Arijit Ukil, Kolkata (IN); Soma Bandyopadhyay, Kolkata (IN); Chetanya Puri, Kolkata (IN); Rituraj Singh, Kolkata (IN); Arpan Pal, Kolkata (IN); Debayan Mukherjee, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 1020 days.

(21) Appl. No.: 15/828,540

(22) Filed: Dec. 1, 2017

(65) Prior Publication Data
US 2018/0153419 A1 Jun. 7, 2018

(30) Foreign Application Priority Data
Dec. 2, 2016 (IN) .............................. 201621041324

(51) Int. Cl.
| | |
|---|---|
| *A61B 5/024* | (2006.01) |
| *G16H 50/20* | (2018.01) |
| *G06F 16/783* | (2019.01) |
| *A61B 34/10* | (2016.01) |
| *A61B 7/04* | (2006.01) |
| *H04R 29/00* | (2006.01) |

(52) U.S. Cl.
CPC ...... *A61B 5/02405* (2013.01); *A61B 5/02444* (2013.01); *A61B 7/04* (2013.01); *A61B 34/10* (2016.02); *G06F 16/7834* (2019.01); *G16H 50/20* (2018.01); *H04R 29/00* (2013.01)

(58) Field of Classification Search
None
See application file for complete search history.

(56) References Cited

U.S. PATENT DOCUMENTS

2014/0207765 A1 7/2014 Haws et al.

OTHER PUBLICATIONS

Yildirim, P. (Aug. 2015). "Filter Based Feature Selection Methods for Prediction of Risks in Hepatitis Disease," *International Journal of Machine Learning and Computing*, vol. 5, No. 4; pp. 258-263.
Robnik-Šikonja, M. et al. (Oct. 2003). "Theoretical and Empirical Analysis of ReliefF and RReliefF," *Machine Learning Journal*, vol. 53, issue 1-2; pp. 23-69.
Shorten, G. et al. (Jun. 2011). "Pre-Processing for Value Based Dynamic Time Warping of the ECG Signal," *ISSC 2011, Trinity College Dublin*; 6 pages.

*Primary Examiner* — G Steven Vanni
(74) *Attorney, Agent, or Firm* — Finnegan, Henderson, Farabow, Garrett & Dunner, LLP

(57) ABSTRACT

This disclosure relates generally to physiological monitoring, and more particularly to feature set optimization for classification of physiological signal. In one embodiment, a method for physiological monitoring includes identifying clean physiological signal training set from an input physiological signal based on a Dynamic Time Warping (DTW) of segments associated with the physiological signal. An optimal features set is extracted from a clean physiological signal training set based on a Maximum Consistency and Maximum Dominance (MCMD) property associated with the optimal feature set that strictly optimizes on the objective function, the conditional likelihood maximization over different selection criteria such that diverse properties of different selection parameters are captured and achieves Pareto-optimality. The input physiological signal is classified into normal signal components and abnormal signal components using the optimal features set.

13 Claims, 3 Drawing Sheets

SYSTEM AND METHOD FOR PHYSIOLOGICAL MONITORING AND FEATURE SET OPTIMIZATION FOR CLASSIFICATION OF PHYSIOLOGICAL SIGNAL

PRIORITY CLAIM

This U.S. patent application claims priority under 35 U.S.C. § 119 to: India Application No. 201621041324, filed on Dec. 2, 2016. The entire contents of the aforementioned application are incorporated herein by reference.

TECHNICAL FIELD

This disclosure relates generally to physiological monitoring, and more particularly to feature set optimization for classification of physiological signal.

BACKGROUND

Healthcare data is quite rich and often contains human survival related information. Analyzing healthcare data is of prime importance, particularly considering the immense potential of saving human life and improving quality of life. An important insight that plays a prominent role in healthcare analytics is anomaly detection. For instance, healthcare analytics can provide insights regarding health of a subject's heart by proactive monitoring of cardiac health. The automated healthcare analytics is based on selection of features corresponding to healthcare related data for building robust classification models. Providing relevant features as input to the classification models can improve model interpretation, robustness, accuracy, speeds up the learning process, reduces the cost of storage and increases generalization capability of the analytics models.

In conventional feature selection methods, the features are ranked in order of closeness to satisfy feature selection criteria for selecting features. However, in certain scenarios, the ranking may not provide a list of most useful features. Moreover, the conventional techniques lack focus on the definite feature sets which provides a maximum probability of predicting accurate outcome. Also, in most of the conventional techniques, extensive human intervention is required, thereby rendering the feature selection process cumbersome and inefficient. In addition, currently automated healthcare analytics for proactive cardiac health monitoring faces certain challenges, particularly for example in Phonocardiogram (PCG) signals based proactive cardiac health monitoring. For instance, the PCG signals frequently includes varying levels of corruption/noise due to presence of multiple noise sources such as motion artefacts, ambient noise.

SUMMARY

Embodiments of the present disclosure present technological improvements as solutions to one or more of the above-mentioned technical problems recognized by the inventors in conventional systems. For example, in one embodiment, a a processor-implemented method for physiological monitoring is provided. The method includes identifying a clean physiological signal training set from an input physiological signal based on a Dynamic Time Warping (DTW) of a plurality of segments associated with the physiological signal, via one or more hardware processors. Further, the method includes extracting an optimal feature set from the clean physiological signal training set, based on a Maximum Consistency and Maximum Dominance (MCMD) property associated with the optimal feature set, via the one or more hardware processors. The MCMD property strictly optimizes on an objective function associated with conditional likelihood maximization over a plurality of selection parameters so that diverse properties of the plurality of selection parameters are captured in optimizing the objective function. Furthermore, the method includes classifying the input physiological signal into normal signal components and abnormal signal components using the optimal feature set, via the one or more hardware processors.

In another embodiment, a system for physiological monitoring is provided. The system includes one or more memories storing instructions; and one or more hardware processors coupled to the one or more memories. The one or more hardware processors are configured by said instructions to identify a clean physiological signal training set from an input physiological signal based on a Dynamic Time Warping (DTW) of a plurality of segments associated with the physiological signal. Further, one or more hardware processors are configured by said instructions to extract an optimal features set from the clean physiological signal training set based on a Maximum Consistency and Maximum Dominance (MCMD) property that derives the optimal feature set. The MCMD property strictly optimizes on an objective function associated with conditional likelihood maximization over a plurality of feature selection parameters so that diverse properties of the plurality of feature selection parameters are captured in optimizing the objective function. Furthermore the one or more hardware processors are configured by said instructions to classify the input physiological signal into normal signal components and abnormal signal components using the optimal feature set.

In yet another embodiment, a non-transitory computer-readable medium having embodied thereon a computer program for executing a method for physiological monitoring is provided. The method includes identifying a clean physiological signal training set from an input physiological signal based on a Dynamic Time Warping (DTW) of a plurality of segments associated with the physiological signal, via one or more hardware processors. Further, the method includes extracting an optimal feature set from the clean physiological signal segment training set based on a Maximum Consistency and Maximum Dominance (MCMD) property derived from the optimal feature set, via the one or more hardware processors. The MCMD property strictly optimizes on an objective function associated with conditional likelihood maximization over a plurality of feature selection parameters so that diverse properties of the plurality of feature selection parameters are captured in optimizing the objective function. Furthermore, the method includes classifying the input physiological signal into normal signal components and abnormal signal components using the optimal feature set, via the one or more hardware processors.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary

DETAILED DESCRIPTION

Figure 1:
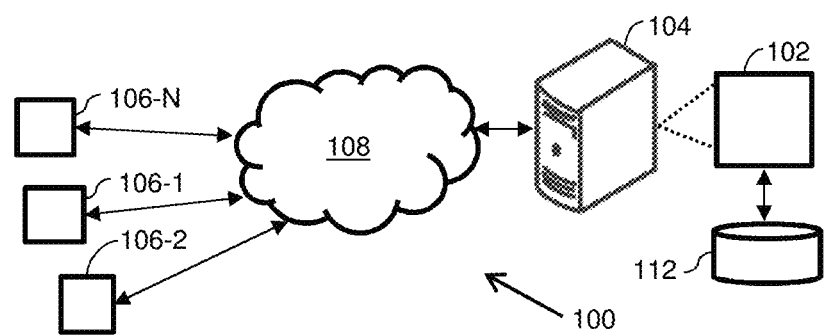
FIG. 1 illustrates a networking environment implementing physiological monitoring according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Auscultation based heart sound/Phonocardiogram (PCG) analysis is a basic test performed by healthcare providers to evaluate heart condition of a subject. Changes in heart sounds and murmurs may occur prior to other cardiovascular symptoms. Hence, cardiac anomalous condition detection can be performed by using one or more acoustic signals, such as PCG signals.

Conventionally, analysis of PCG signals for cardiac event detection gives low accuracy. One of the primary causes for said low accuracy is attributed to presence of noise in PCG signals. For instance, sources such as external noise source, respiration of the subject, and so on corrupt the PCG signal. Especially in practical setup, higher false alarms in PCG signal analysis is attributed to the failure to identify noisy PCG. Conventional classification techniques indicate cardiac abnormality detection from the PCG signals ignoring the impact of noise. Another challenge with utilizing the PCG signals for physiological monitoring is to find an optimal feature set. The optimal feature set is relative to certain criterion. For different types of criteria or feature selection parameters, different optimal feature set is obtained. However, obtaining an optimal feature set of classification of the PCG signals is challenging.

Various embodiments of the present disclosure provide method and system that may facilitate in effective classification of physiological signals such that the above mentioned disadvantages of the conventional physiological signal monitoring and classification systems can be negated. For example, the disclosed system denoises the PCG signal before performing the classification, thereby eliminating artefacts and false-positives from the PCG signal. In an embodiment, the system differentiates between noisy and clean PCG signals, and subsequently denoises the PCG signal.

Additionally, the disclosed system eliminates dependency of optimal feature set to a single feature selection criteria or parameter function, and ensures generalized feature selection criteria/parameter. In particular, the disclosed system identifies most consistent, as well as important feature set from an array of criteria/parameter functions for performing the classification. In an embodiment, the system incorporates a filter approach, called as called Maximum Consistency Maximum Dominance (MCMD), for optimal feature selection. MCMD is maximally supreme in their consistency property to clearly identify the target class C={normal; abnormal}, as will be described later in the description. The MCMD property strictly optimizes on an objective function associated with conditional likelihood maximization over a plurality of feature selection parameter so that diverse properties of the plurality of feature selection parameter are captured in optimizing the objective function.

Due to the above mentioned embodiments, the system and method facilitates in identification of cardiac abnormality from PCG signals with a high accuracy of approximately more than 85%. It will be worth mentioning that the disclosed method operates in an automatic manner, i.e. without any human-in-loop. A detailed description of the above described system for physiological monitoring is presented with respect to illustrations represented with reference to FIGS. 1 through 5.

The method(s) and system(s) for physiological monitoring are further described in conjunction with the following figures. It should be noted that the description and figures merely illustrate the principles of the present subject matter. It will thus be appreciated that those skilled in the art will be able to devise various arrangements that, although not explicitly described or shown herein, embody the principles of the present subject matter and are included within its spirit and scope. Furthermore, all examples recited herein are principally intended expressly to be only for pedagogical purposes to aid the reader in understanding the principles of the present subject matter and the concepts contributed by the inventor(s) to furthering the art, and are to be construed as being without limitation to such specifically recited examples and conditions. Moreover, all statements herein reciting principles, aspects, and embodiments of the present subject matter, as well as specific examples thereof, are intended to encompass equivalents thereof.

FIG. 1 illustrates a network environment 100 implementing a system 102 for physiological monitoring, according to an embodiment of the present subject matter. In an embodiment, the system 102 receives sensor data from one or more sensors that are capable of monitoring subject's physiological health. Examples of the one or more sensors include, but are not limited to, Smartphone inbuilt sensors, digital stethoscope, and acoustic sensor. The system 102 automatically processes the sensor data to perform analysis of the subject's physiological health, and presents result of said analysis on a configurable user interface. The system 102 may be embodied in a computing device, for instance a computing device 104.

Although the present disclosure is explained considering that the system 102 is implemented on a server, it may be understood that the system 102 may also be implemented in a variety of computing systems, such as a laptop computer, a desktop computer, a notebook, a workstation, a cloud-based computing environment and the like. In one implementation, the system 102 may be implemented in a cloud-based environment. It will be understood that the system 102 may be accessed by multiple users through one or more user devices 106-1, 106-2 . . . 106-N, collectively referred to as user devices 106 hereinafter, or applications residing on the user devices 106. Examples of the user devices 106 may include, but are not limited to, a portable computer, a personal digital assistant, a handheld device, a Smartphone, a Tablet Computer, a workstation and the like. The user devices 106 are communicatively coupled to the system 102 through a network 108. Herein, the users of the user-devices 106 may include one or more of the subjects, subject's caregivers, doctors, and so on.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in the computing device 104. Examples of the computing device 104 may include, but are not limited to, a hand-held device, a laptop or other portable computer, a tablet computer, a mobile phone, a PDA, a smartphone, and a desktop computer. The system 102 may also be implemented in a workstation, a server, and a network server. In an embodiment, the system 102 may be coupled to a data repository, for example, a repository 112. The repository 112 may store data processed, received, and generated by the system 102. In an alternate embodiment, the data repository 112 may be embodied within the system 102. The components and functionalities of the system 102 are described further in detail with reference to FIG. 2.

Figure 2:
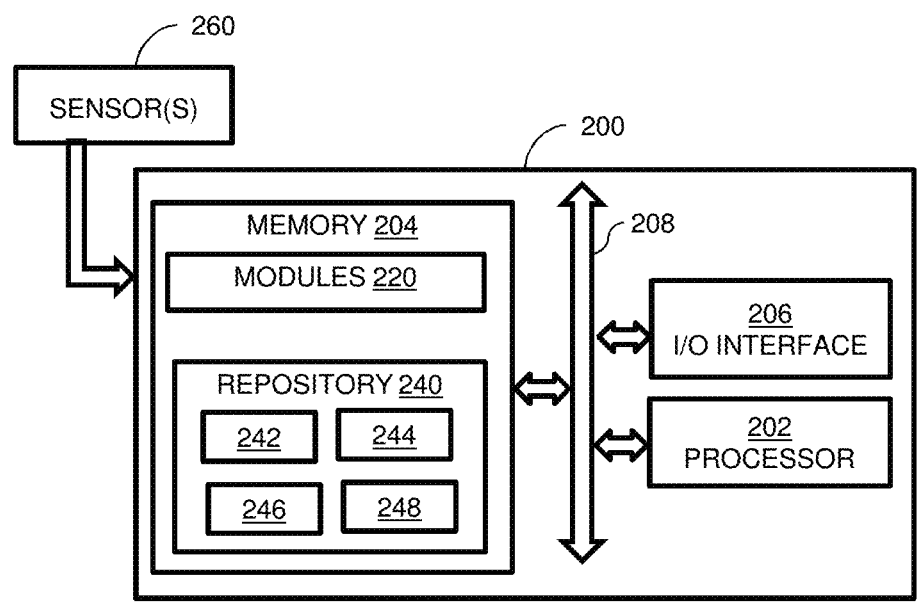
FIG. 2 illustrates a block diagram of physiological monitoring according to some embodiments of the present disclosure.

FIG. 2 illustrates a block diagram of a system performing feature set optimization for audio signal classification 200, in accordance with an example embodiment. The feature set optimization for audio signal classification system 200 (hereinafter referred to as system 200) may be an example of the system 102 (FIG. 1). In an example embodiment, the system 200 may be embodied in, or is in direct communication with the system, for example the system 102 (FIG. 1). The system 200 includes or is otherwise in communication with one or more hardware processors such as a processor 202, at least one memory such as a memory 204, and an I/O interface 206. The processor 202, memory 204, and the I/O interface 206 may be coupled by a system bus such as a system bus 208 or a similar mechanism.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 204.

The I/O interface 206 may include a variety of software and hardware interfaces, for example, a web interface, a graphical user interface, and the like The interfaces 206 may include a variety of software and hardware interfaces, for example, interfaces for peripheral device(s), such as a keyboard, a mouse, an external memory, a camera device, and a printer. Further, the interfaces 206 may enable the system 102 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220. The modules 220 may include routines, programs, objects, components, data structures, and so on, which perform particular tasks or implement particular abstract data types. Additionally, the other modules 220 may include programs or coded instructions that supplement applications and functions of the system 200. The repository 240, amongst other things, includes a system database 242 and other data 244. The other data 244 may include data generated as a result of the execution of one or more modules in the modules 220. Additionally, the repository 240 may include a sensor data 246 and a training data 248. The sensor data 246 may be obtained from one or more sensors 260 employed for physiological sensing of a subject. The training data 248 may be obtained based on training of a classifier for physiological monitoring of, for instance, heart condition of the subject. The details of the sensor data and the training data are explained further in the description below.

Herein, the memory for example the memory 204 and the computer program code configured to, with the hardware processor for example the processor 202, cause the system 200 to perform various functions described herein under.

As discussed above, for physiological monitoring of a subject, the system 200 is caused to monitor physiological signals, such as PCG signals received from the subject. Herein, the physiological signals imbibe properties of audio signals, and may be referred to as audio input signals. Accordingly, the terms 'physiological signals' and 'audio input signals' may be used interchangeably throughout the description.

In an embodiment, the system 200 is caused to identify at least one clean audio signal segment from an input audio signal. In an embodiment, to identify the clean audio signal, the system 200 is caused to segments the input audio signal into a plurality of segments. The system 200 then identifies a clean template segment from the plurality of segments. The clean template segment is associated with noise less than a pre-computed threshold value of noise in the input audio signal. The system 200 then applies DTW to the plurality of segments and calculates DTW distance for each of the plurality of segments. DTW distance measures the intrinsic dissimilarity between the clean segments and the noisy audio segments. It is a semi-supervised technique. The system 200 then selects one or more segments from the plurality of segments as the clean audio signal segments based on a comparison of the DTW distance of the plurality of segments with the DTW distance of the clean template segment. For further clarity, an example of identifying the clean audio signal segment from an input audio signal is explained hereunder by taking PCG signal as example of the input audio signal.

A PCG signal consists of time-series segments, as defined below:

$\psi_i$, i=1, 2, . . . K of S1, Systole, S2, Diastole events,
i.e. $\psi_i$:=[S1; Systole; S2; Diastole]$_i$ The system 200 is caused to identify clean PCG signal segments from the PCG signal, by identifying and isolating clean PCG segments $\Psi_i^{C_1}$ from noisy PCG segments $\Psi_i^{N_1}$. The system 200 identifies the noisy segments $\Psi_i^{N_1}$ and the amount of noisy segments in a PCG signal based on the Dynamic Time Warping (DTW) of the plurality of segments associated with the input audio signal. The DTW facilitates in identifying whether the PCG signal is a noisy or clean. As described previously, DTW distance measures the intrinsic dissimilarity between the clean segments $\Psi_i^{C_1}$ and the noisy segments $\Psi_i^{N_1}$.

The system identifies a clean template segment, T:
T: ={$t_1, t_2, \ldots, t_M$}, where $$M = \frac{60 \times f_s}{HR_{ideal}}$$

is considered.
Here, $f_s$ is sampling frequency and
$HR_{ideal}$ is ideal human heart rate.

The system 200 applies DTW to the PCG signal and computes DTW distance for the plurality of PCG segments. The system 200 compares the DTW distance of the plurality of segments with the DTW distance of the clean template segment Those one or more segments of the PCG signal having the DTW distance greater than the precomputed threshold DTW distance of the template segment may be categorized as noisy physiological PCG segments, while the PCG signal segments having the DTW distance less than or equal to the DTW distance of the ideal segment may be categorized as clean physiological PCG segments. The system 200 may eliminate noisy PCG segments, and store the clean PCG signal segments for further processing. In an embodiment, in order to counter non-linearity in segment lengths, the system 200 computes the most probable segment length $l_p$ of P from the filtered segment series $\Psi_i'$. In an example embodiment, a DBSCAN method may be employed to find the highly likely segment distance set $l_p$ from the set of segment length set $l_i$. DTW distance may be computed between template T and each of the segments $\Psi_i' = \{\omega_1, \omega_2 \ldots \omega_{l_p}\} i, i \forall K$ The system 200 is caused to extract a set of optimal features from the clean audio signal segments (for instance, the clean PCG signal segments). The system 200 extracts the set of optimal feature from the clean audio signal segments based on Maximum Consistency and Maximum Dominance (MCMD) attributes associated with the optimal feature set. As will be appreciated from later description herein, MCMD attributes provides the optimal feature set that optimizes the objective function of conditional likelihood maximization. MCMD strictly optimizes on the objective function (conditional likelihood maximization) over different feature selection parameter like minimum Redundancy Maximum Relevance (mRMR), Mutual Information Feature Selection (MIFS), Conditional Infomax Feature Extraction (CIFE), Interaction Capping (ICAP), Conditional Redundancy (CONDRED), Joint Mutual Information (JMI), CMIM, Double Input Symmetrical Relevance (DISR) such that diverse properties of different feature selection parameter are captured.

In order to extract the MCMD attributes from the clean audio signal segments, the system 200 is caused to identify a plurality of features from the clean audio segments. For example, 'F' may be an initial feature set containing the plurality of features of the clean audio segments. Examples of the plurality of features include, but are not limited to, temporal, wavelet and spectral domains like kurtosis, wavelet co-efficient, PCG R-peak to R-peak duration, The system 200 selects the optimal feature set from the initial feature set that maximizes the probability of predictive accuracy outcome. To select the optimal features set, the system 200 assigns a rank to each of the plurality features based on a plurality of feature selection parameter. The system 200 calculates, for a plurality of feature pairs selected from the plurality of features, a plurality of rank-distances between corresponding ranks. In an embodiment, a rank-distance of the plurality of rank-distances between features of a feature pair of the plurality of feature pairs is defined by Manhattan distance. The system 200 identifies a set of maximum consistent features from the plurality of features based on a comparison of the rank-distances of the plurality of rank-distances with a consistency threshold.

In an embodiment, the system 200 identifies the set of maximum consistent features by selecting the consistency threshold, and identifying the features in the maximum consistent features having rank-distance less than or equal to the consistency threshold for more than half of the plurality of selection parameters. Herein, the consistency threshold is less than or equal to a number of selection parameters.

The system 200 identifies a set of maximum dominance features from the set of maximum consistent features based on a comparison of the ranks of the plurality of Manhattan distances with a dominance threshold. In an embodiment, the system 200 identifies the set of maximum dominance features from the set of maximum consistent feature set by selecting the dominance threshold, and identifies the set of maximum dominance features as the features having the ranks greater than the dominance threshold from the set of maximum consistent feature. Herein, the dominance threshold is less than or equal to number of features in the initial feature set. The optimal feature set or the set of MCMD features is a subset of the plurality of feature, the set of maximum consistent features and the set of maximum dominance features, and is present in both the set of maximum consistent features and the set of maximum dominance features. In an embodiment, the optimal feature set is identified from the plurality of features based on a determination of feature set that is consistently ranked with ranks greater than the ranks associated with the dominance threshold for the plurality of feature selection parameters.

An example of the selection of the optimal feature set based on the MCMD attributes is described further in detail below.

In the present example, let $\Theta = \{\theta_1, \theta_2, \ldots, \theta_z\}$ be the z number of features of the given data set D, and
Feature Selection parameter or Criteria $J \subset \Upsilon = \{$ICAP, JMI, DISR, CONDRED, mRMR, MIFS, CIFE, CMIM$\}$, where $\Upsilon$ is the set of all the feature selection criteria available.

Feature selection method $\Upsilon$ selects Q, Q ⊂ Θ, where p be the cardinality of Q, p≤z, following the MCMD criteria:

$$MC_{property}:\max(U(Q,C/J)), U=\lambda_{(\theta_1,\theta_2\ldots\theta_{p'})}(C) \quad (1)$$

Where $U=\lambda_{(\theta_1,\theta_1\ldots\theta_1)}$ (C) represents the consistency between feature subset Q and the target class label C, over the conditional likelihood probability l(x;y) for a large set of feature selection criteria/parameter J(ICAP, JMI, DISR, CONDRED, mRMR, MIFS, CIFE, CMIM).

$$MD_{property}:\max(V(Q,C/J)), V=\beta_{(\theta_1,\theta_2\ldots\theta_{p'})}(C) \quad (2)$$

Where $\beta_{(\theta_1,\theta_2\ldots\theta_{p'})}$ (C) represents the dominance between feature subset Q and the target class label C, over the conditional likelihood probability l(x;y) for a large set of feature selection criteria/parameter J(ICAP, JMI, DISR, CONDRED, mRMR, MIFS, CIFE, CMIM). The feature set QMCMD is said to be satisfying MCMD property, for which each of the features $\theta_i$, i=1, 2, . . . , p'; p'≤z, has the following condition satisfied:

$$\text{MCMD property: } \theta_i \in Q_{MC} \wedge Q_{MD} \rightarrow \theta_i \in Q_{MCMD} \quad (3)$$

From the above example, $\theta_i \in Q_{MCMD}$; $\theta_2 \notin Q_{MCMD}$. For each J, each of the features in Θ has unique ranks up to z, i.e. Θ transforms to a vector of dimension j, where j be the total number of feature selection criteria/parameter in J, $\Theta \rightarrow \Theta^j$, $\theta_i \rightarrow \theta_i^j$, i=1, 2, . . . z. The objective of MCMD is to find Q, $\Theta^j \rightarrow Q$ for which both eqn. 1 and 2 are satisfied. MCMD property achieves Pareto-optimality so that no other criterion in J achieves both higher dominance and consistency than Q, which means Q performs better in terms of efficacy than any of $\Theta^j$ for a given classifier.

Let u, v be the dominance and consistency threshold respectively, where u is defined as a specific given positive real number ≤z such that each of the features in Maximum Dominance (MD) feature set $Q_{MD}$ satisfies that its rank is ≤u for majority of the feature selection criteria/parameter, i.e. all the features in $Q_{MD}$ has rank ≤u in at least [j/2] number of feature selection criteria/parameter in J. For example, rank of $\theta_1$ be $$r_{(j=ICAP,JMI,DISR,CONDRED,mRMR,MISF,CIFE,CMIM)}^1 = \{2, 6, 10, 5, 3, 2, 1, 2\}$$

Where initial feature size z=54 and total number of feature selection criteria/parameter j=8 and rank of $\theta_2$ be $$r_{(j=ICAP,JMI,DISR,CONDRED,mRMR,MISF,CIFE,CMIM)}^2 = \{10, 2, 30, 18, 21, 13, 4, 26\},$$

given u=10. In this case, $\theta_1$ satisfies MD property, $\theta_1 \in Q_{MD}$, $\theta_2 \notin Q_{MD}$ does not.

Consistency threshold v is defined as a specific given positive real number ≤j such that each of the features in Maximum Consistency (MC) feature set QMC satisfies that its rank-distance r is ≤v for majority of the feature selection criteria, i.e. all the features in QMC has r≤v in at least [j/2] number of feature selection criteria in J, where rank-distance is the Minkowski distance of order 1 (Manhattan distance) between the ranks of selection criteria. For example, rank-distance $\theta_1$ between ICAP-JMI feature selection criteria is 4 as $r_{(j=ICAP,JMI,DISR)}^1 = \{2, 6, 10\}$. From the above example with $\theta_1$, $\theta_2$; $\theta_1$ satisfies Maximum Consistency property $\theta_1 \in Q_{MC}$, $\theta_2 \notin Q_{MC}$, given v=3. Let the rank of $\theta_3$ be:

$$r_{(j=ICAP,JMI,DISR,CONDRED,mRMR,MISF,CIFE,CMIM)}^3 = \{12, 13, 4, 11, 12, 14, 11, 13\},$$

given u=10; v=3, $\theta_3 \in Q_{MC}$; $\theta_3 \notin Q_{MD} \rightarrow \theta_1 \in Q_{MCMD}$; $\theta_2$, $\theta_3 \notin Q_{MCMD}$ The system 200 is caused to classify the input audio signal into normal signal components and abnormal signal components using the MCMD features. In an embodiment, the classification of the physiological audio signal using MCMD feature set may be done as follows: (i) Training a classifier with training data set and (ii) Classifying the input physiological audio signal as normal or abnormal by using the trained classifier. For example, the selected optimal MCMD features are input to a non-linear Support Vector Machine (SVM) classifier with radial basis function (RBF) kernel. The SVM classifier classifies the abnormalities in PCG signal automatically. In an embodiment, the classifier can be utilized for identification of cardiac abnormality of a subject.

In an exemplary embodiment, the physiological audio signal is described to include the PCG signal. Herein, it will be noted that the PCG signal is considered as only an example of the physiological audio signal for the brevity of the description, however in alternative embodiments, the examples of physiological audio signal may include various other such signal such as heart sound and so on.

In an embodiment, the system The PCG signal of the subject undergoing the test is collected and given to the system 200. The system 200 identifies the noisy PCG segments using DTW algorithm and discards it. The clean PCG signal segments are given to the MCMD feature selection module and the optimal MCMD features are selected. The selected optimal MCMD features are input to a non-linear Support Vector Machine (SVM) classifier with radial basis function kernel. The SVM classifier classifies the abnormalities in PCG signal automatically.

Figure 3:
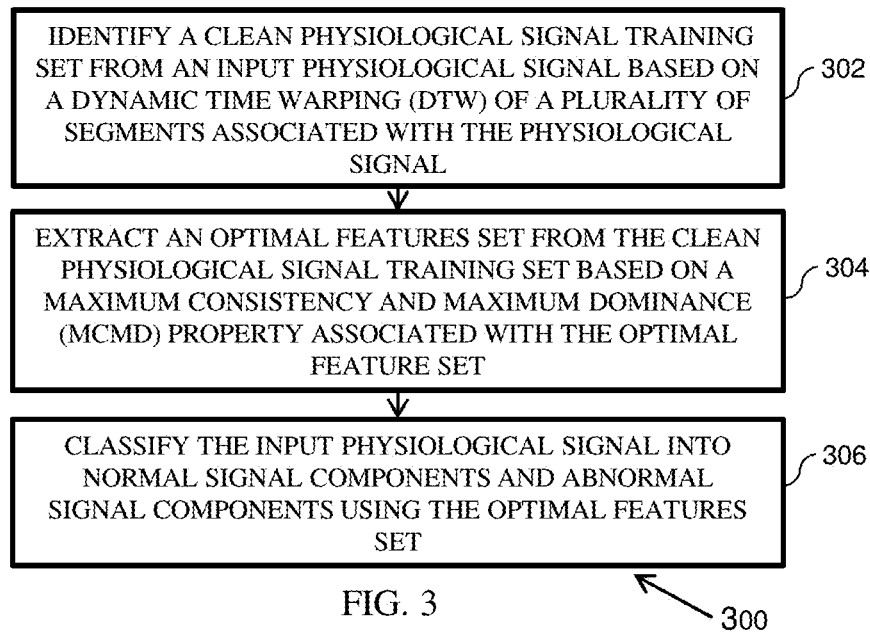
FIG. 3 illustrates an example process flow for physiological monitoring according to some embodiments of the present disclosure.

FIG. 3 illustrates a flow-diagram of a method 300 for physiological monitoring, in accordance with example embodiment. The method 300 may be described in the general context of computer executable instructions. Generally, computer executable instructions can include routines, programs, objects, components, data structures, procedures, modules, functions, etc., that perform particular functions or implement particular abstract data types. The method 300 may also be practiced in a distributed computing environment where functions are performed by remote processing devices that are linked through a communication network. The order in which the method 300 is described is not intended to be construed as a limitation, and any number of the described method blocks can be combined in any order to implement the method 300, or an alternative method. Furthermore, the method 300 can be implemented in any suitable hardware, software, firmware, or combination thereof. In an embodiment, the method 300 depicted in the flow chart may be executed by a system, for example, the system 200 of FIG. 2. In an example embodiment, the system 200 may be embodied in a computing device, for example, the computing device 110 (FIG. 1).

In an embodiment, the system may receive an input physiological signal from one or more sensors, via one or more hardware processors such as the processor 202. The input physiological signal may include physiological audio signals obtained from a subject. At 302, the method 300 includes, identifying at least one clean physiological signal segment from an input physiological signal based on a Dynamic Time Warping (DTW) of a plurality of segments associated with the physiological signal. In an embodiment, identifying the clean physiological signal segment includes segmenting the input physiological signal into a plurality of segments, and identifying a clean template segment from the plurality of segments. The clean template segment is associated with a noise level less than a pre-computed threshold level of noise in the input physiological signal. DTW is applied to the plurality of segments and a DTW distance is calculated for each of the plurality of segments. At least one segment is selected from the plurality of segments as the at least one clean physiological signal segment based on a comparison of the DTW distance of the plurality of segments with the DTW distance of the clean template segment.

At 304, the method 300 includes, extracting an optimal features set from the a clean physiological signal training set based on a Maximum Consistency and Maximum Dominance (MCMD) property associated with the optimal feature set, via the one or more hardware processors such as the processor 202. As described previously, the MCMD property of the optimal feature set strictly optimizes on the objective function (conditional likelihood maximization) over different selection criteria like mRMR, MIFS, CIFE, ICAP, CONDRED, JMI, CMIM, DISR such that diverse properties of different feature selection criteria are captured. MCMD achieves Pareto-optimality so that no other criterion in ⌡ achieves both higher dominance and consistency than ℭ, which means ℭ performs better in terms of efficacy than any of Θ$^j$ for a given classifier. In an embodiment, extracting the optimal features set from the at least one clean audio signal segment includes identifying a plurality of features associated with the at least one clean physiological segment, and a plurality of feature selection parameters, and assigning rank to each of the plurality features based on the plurality of feature selection parameters. For a plurality of feature pairs selected from the plurality of features, a plurality of rank-distances between corresponding ranks are calculated. In an embodiment, rank-distance of the plurality of rank-distances between features of a feature pair of the plurality of feature pairs defined by Manhattan distance. A set of maximum consistent features is identified from the plurality of features based on a comparison of the rank-distances of the plurality of rank-distances with a consistency threshold. Further, a set of maximum dominance features is identified from the set of maximum consistent features based on a comparison of the rank-distances of the plurality of rank-distances with a dominance threshold. The optimal feature set or the set of MCMD features is a subset of the plurality of feature, the set of maximum consistent features and the set of maximum dominance features, and is present in both the set of maximum consistent features and the set of maximum dominance features. In an embodiment, the optimal feature set is identified from the plurality of features based on a determination of feature set that is consistently ranked with ranks greater than the ranks associated with the dominance threshold for the plurality of feature selection parameters.

At 306, the method 300 includes, classifying the input physiological signal into normal signal components and abnormal signal components using the optimal features set, via the one or more hardware processors such as the processor 202. In an embodiment, the classification of the physiological audio signal using the optimal features set (or the MCMD feature set) may be done as follows: (i) Training a classifier with training data set and (ii) Classifying the input physiological audio signal as normal or abnormal by using the trained classifier. For example, the selected optimal MCMD features are input to a non-linear Support Vector Machine (SVM) classifier with radial basis function (RBF) kernel. The SVM classifier classifies the abnormalities in PCG signal automatically.

In an example embodiment, the disclosed physiological monitoring system 200 is tested with publicly available large PCG database. Classical feature selection methods like CMIM were selected along with handpicked methods to compare with the accuracy of the the disclosed system. The handpicked features included selected feature set from temporal, wavelet and spectral domains. Accuracy of identifying the noisy PCG signals from an example data set (for instance a Physionet Challenge 2016 data set) is 84% as shown in FIG. 6. As an example, 54 exhaustive features 'F'=$\{f_1, f_2, \ldots, f_{54}\}$ from temporal, spectral and wavelet domains are selected, the value of u is taken as 20 and the value of v is taken as 3. The ranks calculated for the features of the initial feature set using the feature selection parameters of 'Z' is shown in FIG. 4.

Figure 4:
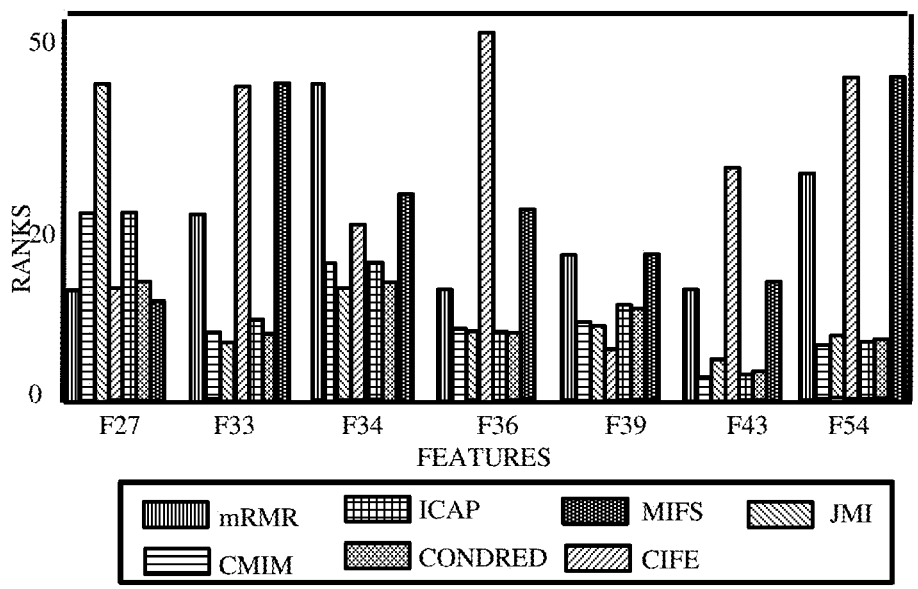
FIG. 4 illustrates an example graph showing ranking of features calculated using various ranking methods according to some embodiments of the present disclosure.
Figure 5:
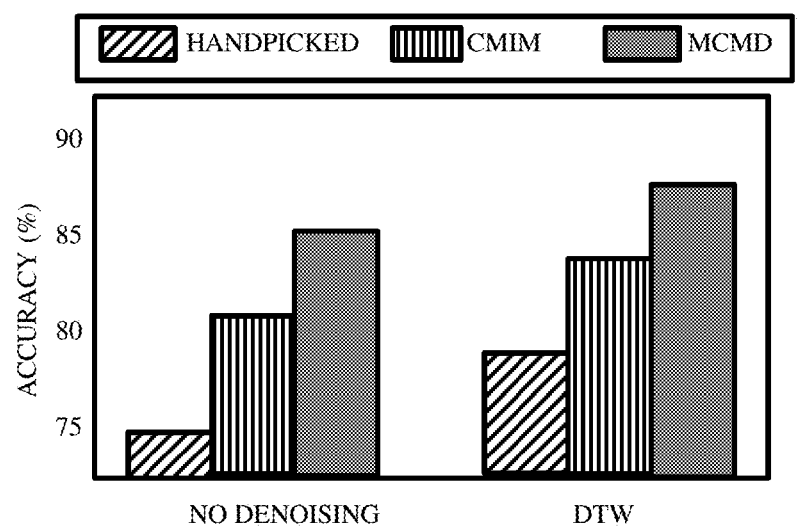
FIG. 5 illustrates an example graph showing accuracy of noisy and clean signal classification using Dynamic Time Warping (DTW) according to some embodiments of the present disclosure.

It is shown that 7 features satisfy MCMD property i.e $\theta_i \in Q_{MCMD}$, i=$\{27; 33; 34; 36; 39; 43; 54\}$ as depicted in FIG. 4, $F_v$, v represents feature. In FIG. 5, the performance efficacy of our disclosed system is represented on the total datasets consisting of separate Training (Normal #716, Abnorma #312) and Testing (Normal #1772, Abnormal #353). following the protocol of FIG. 4. Two important observations that can be derived from the experimental results are: 1. Denoising ensures better performance. Around 10% accuracy gain is achieved through denoising. 2. MCMD feature selection outperforms CMIM or handpicked feature selection by more than 6%.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for physiological monitoring, the method comprising:
identifying a clean physiological signal training set from an input physiological signal based on a Dynamic Time Warping (DTW) of a plurality of segments associated with the physiological signal, via one or more hardware processors, wherein the input physiological signal is received from one or more sensors that are capable of monitoring subject's physiological health including smartphone inbuild sensors, a digital stethoscope, and an acoustic sensor, wherein the input physiological signal comprises a physiological audio signal obtained from a subject and the physiological audio signal includes a phonocardiogram (PCG) signal, wherein identifying the clean physiological signal training set comprises:
segmenting the input physiological signal into a plurality of segments, via the one or more hardware processors;
identifying a clean template segment from the plurality of segments, via the one or more hardware processors, the clean template segment associated with a noise level less than a pre-computed threshold level of noise in the input physiological signal;
applying a DTW algorithm on the plurality of segments to calculate DTW distance between each of the plurality of segments and the clean template segment, via the one or more hardware processors; and
selecting at least one segment from the plurality of segments as a clean physiological signal segment of the clean physiological signal training set based on a comparison of the DTW distance of the plurality of segments with a pre-computed DTW threshold distance, via the one or more hardware processors, wherein the DTW distance measures an intrinsic dissimilarity between the clean physiological signal segment and the noisy physiological signal segment as a semi-supervised technique, wherein a segment from the plurality of segments having the DTW distance greater than the pre-computed DTW threshold distance is categorized as a noisy physiological signal segment and discards the noisy physiological signal segment, wherein the differentiation between the noisy physiological signal segment and the clean physiological signal segment facilitates denoising the PCG signal before performing classification and results in eliminating artefacts and false-positives from the PCG signal, and wherein a segment from the plurality of segments having the DTW distance less than or equal to the pre-computed DTW threshold distance is categorized as the clean physiological signal segment;
extracting an optimal feature set from the clean physiological signal training set based on a Maximum Consistency and Maximum Dominance (MCMD) property associated with the optimal feature set, via the one or more hardware processors using an MCMD feature selection module, the MCMD property is maximally supreme in their consistency property to clearly identify a target class C={normal; abnormal}, and the MCMD property strictly optimizes on an objective function associated with conditional likelihood maximization over a plurality of feature selection parameters so that diverse properties of the plurality of feature selection parameters are captured, wherein the optimal feature set is a subset of the plurality of features, a set of maximum consistent features and the set of maximum dominance features, and present in both the set of maximum consistent features and the set of maximum dominance features; and
classifying the input physiological signal into normal signal components and abnormal signal components using the optimal features set by (i) training a classifier with training data set, and (ii) classifying the input physiological signal as normal or abnormal using the trained classifier, and further the optimal feature set is input to a non-linear Support Vector Machine (SVM) classifier with radial bias function (RBF) kernel, wherein the SVM classifier classifies the abnormalities in the PCG signal automatically without human intervention, wherein the classifier is utilized for identification of cardiac abnormality of the subject from the PCG signal with an accuracy of approximately more than 85%.

2. The method of claim 1, wherein extracting the optimal features set from the at least one clean audio-physiological signal segment comprises:
identifying a plurality of features associated with the clean physiological signal training set, and a plurality of feature selection parameters;
assigning rank to each of the plurality features based on the plurality of feature selection parameters;
calculating, for a plurality of feature pairs selected from the plurality of features, a plurality of rank-distances between corresponding ranks, a rank-distance of the plurality of rank-distances between features of a feature pair of the plurality of feature pairs defined by Manhattan distance;
identifying the set of maximum consistent features from the plurality of features based on a comparison of the rank-distances of the plurality of rank-distances with a consistency threshold; and
identifying the set of maximum dominance features from the set of maximum consistent features based on a comparison of the rank-distances of the plurality of rank-distances with a dominance threshold.

3. The method of claim 2, wherein the plurality of feature selection parameters comprises minimum Redundancy Maximum Relevance (mRMR) parameter, Conditional Mutual Information Maximization (CMIM) parameter, Interaction Capping (ICAP) parameter, Mutual Information Feature Selection (MIFS) parameter, Joint Mutual Information (JMI) parameter, Conditional Infomax Feature Extraction (CIFE) parameter, Double Input Symmetrical Relevance (DISR) parameter, and Conditional Redundancy (CONDRED) parameter.

4. The method of claim 3, wherein identifying the set of maximum consistent features comprises:
selecting the consistency threshold, wherein the consistency threshold is less than or equal to a number of feature selection parameters; and
identifying the set of maximum consistent features as features in the maximum consistent features that have corresponding rank-distance less than or equal to the consistency threshold for more than half of the plurality of feature selection parameters.

5. The method of claim 4, wherein identifying the set of maximum dominance features from the set of maximum consistent feature set comprises:
   selecting the dominance threshold, wherein the dominance threshold is less than or equal to number of features in the plurality of features; and
   identifying, from the set of maximum consistent features, the set of maximum dominance features as features having the rank-distance greater than the dominance threshold.

6. The method of claim 5, further comprising identifying the optimal feature set from the plurality of features based on a determination of feature set that is consistently ranked with ranks greater than the ranks associated with the dominance threshold for the plurality of feature selection parameters.

7. A system for physiological monitoring, the system comprising:
   one or more memories storing instructions; and one or more hardware processors coupled to the one or more memories, wherein said one or more hardware processors are configured by said instructions to:
   identify a clean physiological signal training set from an input physiological signal based on a Dynamic Time Warping (DTW) of a plurality of segments associated with the physiological signal, wherein the input physiological signal is received from one or more sensors that are capable of monitoring subject's physiological health including smartphone inbuild sensors, a digital stethoscope, and an acoustic sensor, wherein the input physiological signal comprises a physiological audio signal obtained from a subject and the physiological audio signal includes a phonocardiogram (PCG) signal, wherein to identify the clean physiological signal training set, the one or more hardware processors are further configured by the instructions to:
   segment the input physiological signal into a plurality of segments;
   identify a clean template segment from the plurality of segments, the clean template segment associated with a noise level less than a pre-computed threshold level of noise in the input physiological signal:
   apply a DTW algorithm on the plurality of segments to calculate DTW distance between each of the plurality of segments and the clean template segment; and
   select at least one segment from the plurality of segments as a clean physiological signal segment of the clean physiological signal training set based on a comparison of the DTW distance of the plurality of segments with a pre-computed DTW threshold distance, wherein the DTW distance measures an intrinsic dissimilarity between the clean physiological signal segment and the noisy physiological signal segment as a semi-supervised technique, wherein a segment from the plurality of segments having the DTW distance greater than the pre-computed DTW threshold distance is categorized as a noisy physiological signal segment and discards the noisy physiological signal segment, wherein the differentiation between the noisy physiological signal segment and the clean physiological signal segment facilitates denoising the PCG signal before performing classification and results in eliminating artefacts and false-positives from the PCG signal, and wherein a segment from the plurality of segments having the DTW distance less than or equal to the precomputed DTW threshold distance is categorized as the clean physiological signal segment;

extract an optimal feature set from the clean physiological signal training set based on a Maximum Consistency and Maximum Dominance (MCMD) property associated with the optimal feature set, using an MCMD feature selection module, the MCMD property is maximally supreme in their consistency property to clearly identify a target class C={normal; abnormal}, and the MCMD property strictly optimizes on an objective function associated with conditional likelihood maximization over a plurality of selection parameters so that diverse properties of the plurality of feature selection parameters are captured, wherein the optimal feature set is a subset of the plurality of features, a set of maximum consistent features and the set of maximum dominance features, and present in both the set of maximum consistent features and the set of maximum dominance features; and
   classify the input physiological signal into normal signal components and abnormal signal components using the optimal features set by (i) training a classifier with training data set, and (ii) classifying the input physiological signal as normal or abnormal using the trained classifier, and further the optimal feature set is input to a non-linear Support Vector Machine (SVM) classifier with radial bias function (RBF) kernel, wherein the SVM classifier classifies the abnormalities in the PCG signal automatically without human intervention, wherein the classifier is utilized for identification of cardiac abnormality of the subject from the PCG signal with an accuracy of approximately more than 85%.

8. The system of claim 7, wherein to extract the optimal features set from the at least one clean physiological signal segment, the one or more hardware processors are further configured by the instructions to:
   identify a plurality of features associated with the clean physiological signal of the training set, and a plurality of feature selection parameters;
   assign rank to each of the plurality of features based on the plurality of feature selection parameters;
   calculate, for a plurality of feature pairs selected from the plurality of features, a plurality of rank-distances between corresponding ranks, a rank-distance of the plurality of rank-distances between features of a feature pair of the plurality of feature pairs defined by Manhattan distance;
   identify the set of maximum consistent features from the plurality of features based on a comparison of the rank-distances of the plurality of rank-distances with a consistency threshold; and
   identify the set of maximum dominance features from the set of maximum consistent features based on a comparison of the rank-distances of the plurality of rank-distances with a dominance threshold.

9. The system of claim 8, wherein the plurality of feature selection parameters comprises minimum Redundancy Maximum Relevance (mRMR) parameter, Conditional Mutual Information Maximization (CMIM) parameter, Interaction Capping (ICAP) parameter, Mutual Information Feature Selection (MIFS) parameter, Joint Mutual Information (JMI) parameter, Conditional Infomax Feature Extraction (CIFE) parameter, Double Input Symmetrical Relevance (DISR) parameter, and Conditional Redundancy (CONDRED) parameter.

10. The system of claim 9, wherein to identify the set of maximum consistent features, the one or more hardware processors are further configured by the instructions to:

select the consistency threshold, wherein the consistency threshold is less than or equal to a number of feature selection parameters; and identify the set of maximum consistent features as features in the maximum consistent features having corresponding rank-distance less than or equal to the consistency threshold for more than half of the plurality of feature selection parameters.

11. The system of claim 10, wherein to identify the set of maximum dominance features from the set of maximum consistent feature set, the one or more hardware processors are further configured by the instructions to:

select the dominance threshold, wherein the dominance threshold is less than or equal to number of features in the plurality of features; and identify the set of maximum dominance features as features having the ranks greater than the dominance threshold from the set of maximum consistent features.

12. The system of claim 11, wherein the one or more hardware processors are further configured by the instructions to identify the optimal feature set from the plurality of features based on a determination of feature set that is consistently ranked with ranks greater than the ranks associated with the dominance threshold for the plurality of feature selection parameters.

13. A non-transitory computer-readable medium having embodied thereon a computer program for executing a method for physiological monitoring, the method comprising:

identifying a clean physiological signal training set from an input physiological signal based on a Dynamic Time Warping (DTW) of a plurality of segments associated with the physiological signal, via one or more hardware processors, wherein the input physiological signal is received from one or more sensors that are capable of monitoring subject's physiological health including smartphone inbuild sensors, a digital stethoscope, and an acoustic sensor, wherein the input physiological signal comprises a physiological audio signal obtained from a subject and the physiological audio signal includes a phonocardiogram (PCG) signal, wherein identifying the clean physiological signal training set comprises:

segmenting the input physiological signal into a plurality of segments:

identifying a clean template segment from the plurality of segments, the clean template segment associated with a noise level less than a pre-computed threshold level of noise in the input physiological signal;

applying a DTW algorithm on the plurality of segments to calculate DTW distance between each of the plurality of segments and the clean template segment; and selecting at least one segment from the plurality of segments as a clean physiological signal segment of the clean physiological signal training set based on a comparison of the DTW distance of the plurality of segments with a pre-computed DTW threshold distance, wherein the DTW distance measures an intrinsic dissimilarity between the clean physiological signal segment and the noisy physiological signal segment as a semi-supervised technique, wherein a segment from the plurality of segments having the DTW distance greater than the pre-computed DTW threshold distance is categorized as a noisy physiological signal segment and discards the noisy physiological signal segment, wherein the differentiation between the noisy physiological signal segment and the clean physiological signal segment facilitates denoising the PCG signal before performing classification and results in eliminating artefacts and false-positives from the PCG signal, and wherein a segment from the plurality of segments having the DTW distance less than or equal to the pre-computed DTW threshold distance is categorized as the clean physiological signal segment;

extracting an optimal feature set from the clean physiological signal training set based on a Maximum Consistency and Maximum Dominance (MCMD) property associated with the optimal feature set, via the one or more hardware processors using an MCMD feature selection module, the MCMD property is maximally supreme in their consistency property to clearly identify a target class C={normal; abnormal}, and the MCMD property strictly optimizes on an objective function associated with conditional likelihood maximization over a plurality of feature selection parameters so that diverse properties of the plurality of feature selection parameters are captured, wherein the optimal feature set is a subset of the plurality of features, a set of maximum consistent features and the set of maximum dominance features, and present in both the set of maximum consistent features and the set of maximum dominance features; and classifying the input physiological signal into normal signal components and abnormal signal components using the optimal features set by (i) training a classifier with training data set, and (ii) classifying the input physiological signal as normal or abnormal using the trained classifier, and further the optimal feature set is input to a non-linear Support Vector Machine (SVM) classifier with radial bias function (RBF) kernel, wherein the SVM classifier classifies the abnormalities in the PCG signal automatically without human intervention, wherein the classifier is utilized for identification of cardiac abnormality of the subject from the PCG signal with an accuracy of approximately more than 85%.

* * * * *